United States Patent
Oka et al.

(10) Patent No.: US 12,193,639 B2
(45) Date of Patent: Jan. 14, 2025

(54) FIBERSCOPE HAVING EXCELLENT INSERTABILITY

(71) Applicant: OK Fiber Technology Co., Ltd., Ibaraki (JP)

(72) Inventors: Kiyoshi Oka, Ibaraki (JP); Sachiko Minakawa, Ibaraki (JP); Yasuo Seki, Hyogo (JP)

(73) Assignee: OK Fiber Technology Co., Ltd., Ibaraki (JP)

( * ) Notice: Subject to any disclaimer, the term of this patent is extended or adjusted under 35 U.S.C. 154(b) by 481 days.

(21) Appl. No.: 17/270,322

(22) PCT Filed: Aug. 26, 2019

(86) PCT No.: PCT/JP2019/033362
§ 371 (c)(1),
(2) Date: Feb. 22, 2021

(87) PCT Pub. No.: WO2020/045362
PCT Pub. Date: Mar. 5, 2020

(65) Prior Publication Data
US 2021/0169311 A1   Jun. 10, 2021

(30) Foreign Application Priority Data

Aug. 29, 2018 (JP) .................................. 2018-160883
Aug. 26, 2019 (JP) .................................. 2019-153903

(51) Int. Cl.
*A61B 1/00* (2006.01)
*A61B 1/07* (2006.01)
(Continued)

(52) U.S. Cl.
CPC ...... *A61B 1/00087* (2013.01); *A61B 1/00133* (2013.01); *A61B 1/00135* (2013.01);
(Continued)

(58) Field of Classification Search
CPC ............ A61B 1/00087; A61B 1/00133; A61B 1/00135; A61B 1/00147; A61B 1/07;
(Continued)

(56) References Cited

U.S. PATENT DOCUMENTS

| | | | |
|---|---|---|---|
| 4,607,622 A | 8/1986 | Fritch et al. | |
| 2004/0236230 A1 | 11/2004 | Crowley et al. | |

(Continued)

FOREIGN PATENT DOCUMENTS

| | | |
|---|---|---|
| CN | 1649537 A2 | 8/2005 |
| CN | 201213784 Y | 4/2009 |

(Continued)

OTHER PUBLICATIONS

International Search Report and Written Opinion for PCT/JP2019/033362 dated Nov. 8, 2019.

(Continued)

*Primary Examiner* — Timothy J Neal
(74) *Attorney, Agent, or Firm* — Christopher M. Scherer; DeWitt LLP

(57) ABSTRACT

The endoscope has an elongated outer tube 2 and an optical element unit 3 provided inside the outer tube 2, the outer tube 2 has an inner layer 21 configured by a soft resin, a reinforcement layer 22 provided outside the inner layer 21, and an outer layer 23 configured by a soft resin covering the reinforcement layer 22; and the optical element unit 3 has an image transmission portion for image transmission 31, a laser transmission portion 32, and a fiber bundle for illumination 33 to fill the space between an inner surface 21a of the inner layer 21, an outer surface 31a of the image transmission portion 31, and an outer surface 32a of the laser transmission portion 32.

4 Claims, 5 Drawing Sheets

(51) Int. Cl.
*A61B 1/267* (2006.01)
*A61B 18/22* (2006.01)
*A61N 5/06* (2006.01)
*A61B 18/00* (2006.01)
*A61N 5/067* (2006.01)

(52) U.S. Cl.
CPC ............ *A61B 1/00147* (2013.01); *A61B 1/07* (2013.01); *A61B 1/2676* (2013.01); *A61B 18/22* (2013.01); *A61N 5/0603* (2013.01); *A61N 5/062* (2013.01); *A61B 2018/00541* (2013.01); *A61B 2018/00577* (2013.01); *A61N 2005/0604* (2013.01); *A61N 2005/0651* (2013.01); *A61N 5/067* (2021.08)

(58) Field of Classification Search
CPC .................. A61B 1/2676; A61B 18/22; A61B 2018/00541; A61B 2018/00577; A61B 1/00167; A61B 1/063; A61N 5/0603; A61N 5/062; A61N 5/067; A61N 2005/0604; A61N 2005/0651
See application file for complete search history.

(56) References Cited

U.S. PATENT DOCUMENTS

| | | | |
|---|---|---|---|
| 2005/0272975 A1 | 12/2005 | McWeeney et al. | |
| 2006/0015009 A1* | 1/2006 | Jaffe | A61B 1/31 600/114 |
| 2008/0275304 A1* | 11/2008 | Barbato | A61B 5/6852 600/160 |
| 2011/0009694 A1* | 1/2011 | Schultz | A61B 10/0233 600/109 |
| 2012/0184818 A1 | 7/2012 | Sugisawa et al. | |
| 2015/0008815 A1 | 3/2015 | Hatta | |
| 2015/0088151 A1* | 3/2015 | Hatta | A61B 17/00234 606/108 |
| 2016/0095507 A1* | 4/2016 | Uram | A61B 1/07 600/108 |
| 2019/0142266 A1* | 5/2019 | Casarotto | A61B 1/07 600/105 |
| 2019/0374095 A1* | 12/2019 | Lord | A61B 1/053 |

FOREIGN PATENT DOCUMENTS

| | | |
|---|---|---|
| CN | 102510740 A | 6/2012 |
| CN | 102599874 A | 7/2012 |
| DE | 3621053 A1 | 1/1988 |
| JP | 62-149301 | 9/1987 |
| JP | 1172801 U | 12/1989 |
| JP | 6-80401 | 11/1994 |
| JP | 2003310551 A | 11/2003 |
| JP | 2007500059 | 1/2007 |
| JP | 2013240409 A | 12/2013 |
| JP | 2015062532 | 4/2015 |
| WO | 03092476 A2 | 11/2003 |
| WO | 2004105598 | 12/2004 |
| WO | 2011037718 A1 | 3/2011 |

OTHER PUBLICATIONS

Office Action issued Jan. 31, 2023, from the Japanese Patent office in connection with corresponding JP Application No. 2019-153903.

Office Action issued Mar. 20, 2023, from the German Patent office in connection with corresponding DE Application 11 2019 004 349.8.

First Office action issued from the Chinese Patent Office on Feb. 29, 2024, in connection with related CN patent application No. 201980053849.6.

* cited by examiner

FIBERSCOPE HAVING EXCELLENT INSERTABILITY

CROSS-REFERENCE TO RELATED APPLICATIONS

The present application is the U.S. national stage application of International Application No. PCT/JP2019/033362, filed Aug. 26, 2019, which international application was published on Mar. 5, 2020, as International Publication No. WO2020/045362. The International Application claims priority to Japanese Patent Application No. 2018-160883, filed Aug. 29, 2018, and Japanese Patent Application No. 2019-153903, filed Aug. 26, 2019, the contents of which are incorporated herein by reference in their entireties.

TECHNICAL FIELD

The invention relates to a fiberscope.

BACKGROUND ART

A laser therapy to irradiate laser light to an affected part is carried out in a cancer therapy using a fiberscope as an endoscope, for example. In this laser therapy, the tip of the endoscope is moved to a target site via a plurality of branch locations of a lumen in the body to irradiate the laser light. For example, in Patent Document 1, a hand operating portion provided on the proximal side of the endoscope is operated to carry out the curving operation of the endoscope at a branch location to make it easy to move the endoscope to the target site.

PRIOR ART DOCUMENT

Patent Document

Patent Document 1: JP 2015-062532 A

SUMMARY OF THE INVENTION

Problem to be Solved by the Invention

However, in a case of an endoscope having a hand operating portion as in Patent document 1, a path for an operating member such as a wire needs to be provided from the hand operating portion (the proximal side of the endoscope) to the tip of the endoscope. In that case, the diameter of the endoscope increases in an amount corresponding to the space to provide the path for the operating member. Moreover, in a case of a structure in which an endoscope is guided along a guide wire, a channel for inserting the guide wire therethrough needs to be provided in the endoscope, increasing the diameter of the endoscope.

In a case that the tip of the endoscope cannot be operated with the hand operating portion or the guide wire, a procedure by a practitioner, such as rotating the endoscope in the circumferential direction of the axis thereof or pushing it in the axial direction thereof, causes the tip of the endoscope to be moved toward a target site. In this case, an insertion portion of the endoscope, such as the tip of the endoscope, which insertion portion thereof is inserted into a lumen, being flexible makes it easy for the endoscope to follow the shape of a route to the target site, the route being three-dimensionally winding. However, when the insertion portion of the endoscope is flexible, adjusting position of the tip of the endoscope at a branch location to the target site becomes difficult.

Thus, in view of such problems, an object of the invention is to provide an endoscope that makes it possible to select a target branched lumen at a branch of a lumen while maintaining the shape without increasing the diameter of the endoscope and adjust position of the tip portion and that makes it possible to curve along a route of the target branched lumen.

Means to Solve the Problem

An endoscope comprises a flexible elongated member having a tip portion and a proximal portion, the flexible elongated member comprising an elongated outer tube to be inserted into a lumen to be observed and an optical element unit provided inside the outer tube, wherein the flexible elongated member has a grip portion provided between the tip portion and the proximal portion, the flexible elongated member has an intermediate portion provided between the tip portion and the grip portion, when a rotating force in a circumferential direction of an axis of the flexible elongated member and a pushing force are applied to the grip portion, the rotating force and the pushing force are transmitted to the tip portion via the intermediate portion to position the tip portion in a predetermined direction, wherein the outer tube has an outer layer mainly containing a resin having flexibility and a reinforcement layer provided inside the outer layer, the optical element unit comprises an image transmission portion for image transmission, a laser transmission portion, and a fiber bundle for illumination, and the flexible elongated member has rigidity capable of selecting a target branched lumen from a branch of the lumen while maintaining the shape and position the tip portion, and flexibility capable of curving along a route to the target branched lumen.

Effects of the Invention

The endoscope according to the invention makes it possible to select a target branched lumen at a branch of a lumen while maintaining the shape without increasing the diameter of the endoscope and adjust position of the tip portion and makes it possible to curve along a route of the target branched lumen.

EMBODIMENT FOR CARRYING OUT THE INVENTION

Below, with reference to the drawings, an endoscope according to one embodiment of the invention is described.

The embodiments shown below are merely exemplary, so that the endoscope according to the invention is not limited to the embodiments below.

Figure 1:
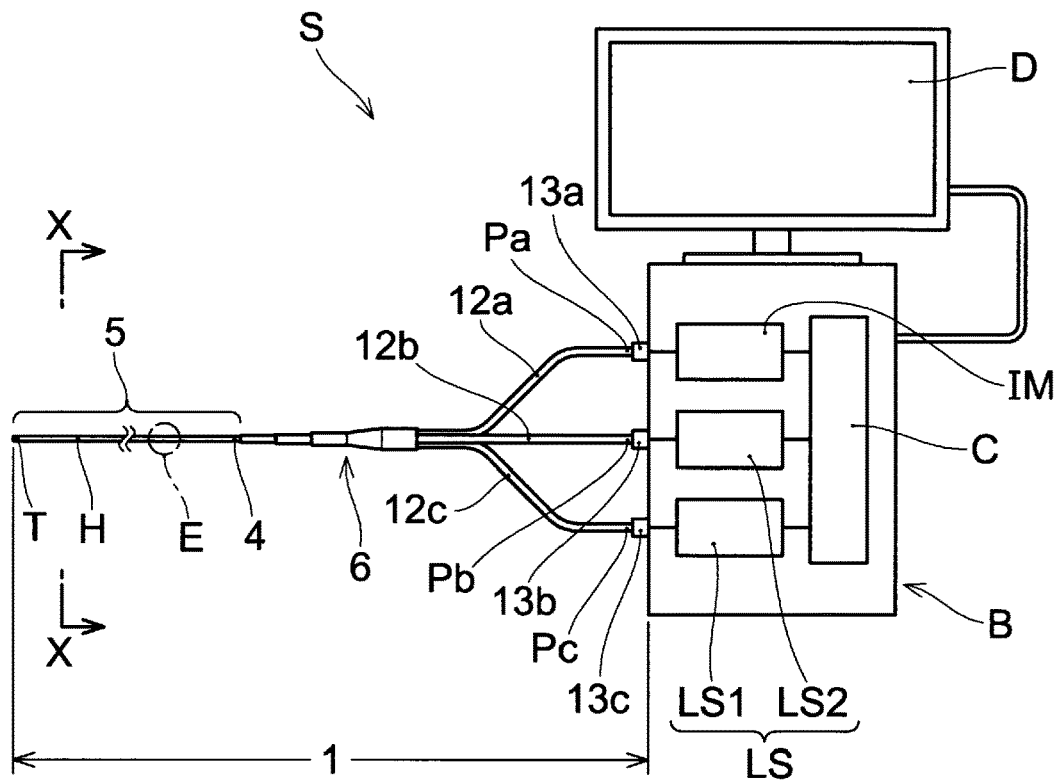
FIG. 1 shows one example of an endoscope system including an endoscope according to one embodiment of the invention.

FIG. 1 shows one example of an endoscope system S comprising an endoscope according to one embodiment of the invention. The endoscope system S is used when carrying out examination and/or therapy for a patient using the endoscope, and, as shown in FIG. 1, comprises an endoscope and a system main body B.

Figure 2:
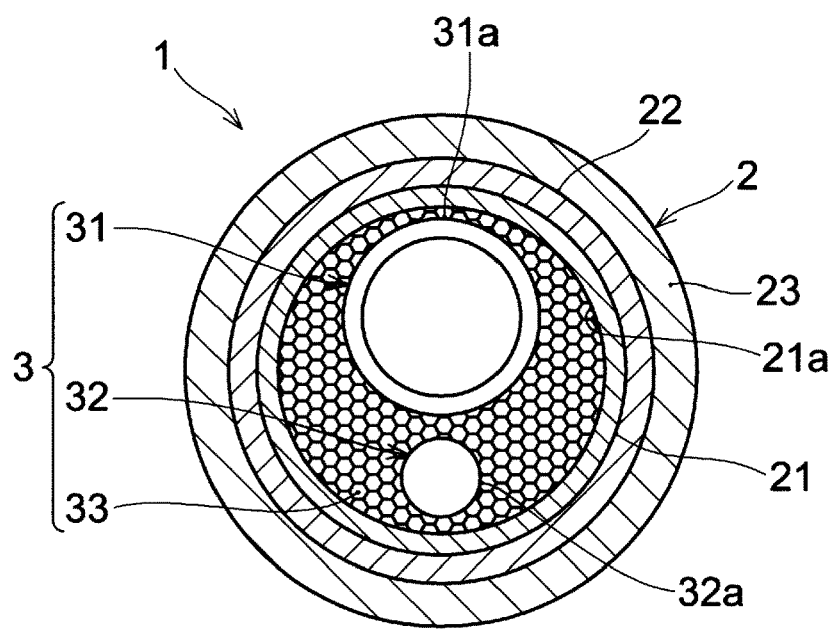
FIG. 2 shows a cross section along X-X in FIG. 1.

A flexible elongated member 1 to be used as an endoscope is inserted into a lumen of the patient and the like, and examination and/or therapy with respect to a target site of the patient is carried out by making a tip portion T of the flexible elongated member 1 reach a target site being a site to be observed such as an affected part or a site to be examined. As shown in FIGS. 1 and 2, the flexible elongated member 1 comprises a tip portion T, a proximal portion P, and an elongated member main body H to be inserted into the lumen. The flexible elongated member 1 comprises an outer tube 2 being elongated, and an optical element unit 3 provided inside the outer tube 2. The optical element unit 3 comprises an image transmission portion for image transmission 31, a laser transmission portion 32, and a fiber bundle for illumination 33. While details are described below, after the flexible elongated member 1 is inserted into a lumen, a target site to be examined is illuminated by light from the fiber bundle for illumination 33, an image of the lumen is transmitted by the image transmission portion 31 to make it possible to check the state of the target site. Laser therapy is carried out by laser light irradiated from the laser transmission portion 32. The laser therapy using the endoscope includes ablation therapy and photodynamic therapy (PDT), for example. In the endoscope in the specification, the outer tube 2 mainly contains a deformable resin having flexibility and comprises a reinforcement layer 22. The tip portion T of the outer tube 2 is deformed according to a curved shape of the lumen and a hand operation for deforming the tip portion T of the outer tube 2 is not performed. While the use of the flexible elongated member 1 is not particularly limited, in the embodiment, the endoscope is an endoscope for examination and/or therapy of the lung to be inserted into a lung peripheral part (a bronchiole, a respiratory bronchiole). Moreover, in another embodiment being different from the invention, the optical element unit 3 may be configured by the image transmission portion 31 and the fiber bundle for illumination 33 without using the laser transmission portion 32, for example. In a case that the laser transmission portion 32 is provided to the endoscope, laser therapy may be carried out.

The overall shape of the flexible elongated member 1 is not particularly limited as long as the flexible elongated member 1 has an effect described below. In the embodiment, the flexible elongated member 1 is inserted into the lumen as shown in FIG. 1. The flexible elongated member 1 comprises the elongated member main body H, three tubes being first to third tubes 12a, 12b, 12c branching from a junction 6 connecting to the elongated member main body H, proximal portions Pa, Pb, Pc of the flexible elongated member 1 provided at the end of the three tubes being the first to third tubes 12a, 12b, 12c, and first to third connectors 13a, 13b, 13c provided at the proximal portions Pa, Pb, Pc, respectively, and connected to the system main body B. The proximal portions Pa, Pb, Pc are collectively called the proximal portion P. For the first to third tubes 12a, 12b, 12c and the first to third connectors 13a, 13b, 13c, an integrated-type connector in which the first to third connectors 13a, 13b, 13c are integrated may be used, or one tube may be used, without dividing into the first to third tubes 12a, 12b, 12c, to provide a singular integrated-type connector at the end of the one tube. The elongated member main body H comprises the outer tube 2 and the optical element unit 3. The optical element unit 3 is separated into members configuring the optical element unit 3 to extend to the proximal portions Pa, Pb, Pc through the first to third tubes 12a, 12b, 12c. The first tube 12a and the first connector 13a connect the image transmission portion 31 to the system main body B. The second tube 12b and the second connector 13b connect the laser transmission portion 32 to the system main body B. The third tube 12c and the third connector 13c connect the fiber bundle for illumination 33 to the system main body B. While the flexible elongated member 1 may be introduced into the lumen without using other members, a bronchoscope may be used as an introduction assisting tool U when the elongated member 1 is introduced into the lumen. In the embodiment, the endoscope does not have a hand operating portion to subject the tip portion T of the flexible elongated member 1 to a curving action on the proximal portion P side of the flexible elongated member 1 and also does not have a physical channel through which a different member such as a guide wire is inserted. The flexible elongated member 1 also does not have an operating wire for operation to connect the hand operating portion and the tip portion T. Details of the endoscope will be described below.

The system main body B is a device to which the flexible elongated member 1 is connected and is to be an illumination light source and a laser light source of the endoscope. The system main body B processes an image imaged by the endoscope. In the embodiment, as shown in FIG. 1, the system main body B has a display device D, an imaging device IM, and a light source device LS. Moreover, the system main body B has a control device C and carries out various controls needed for illumination, imaging, and laser therapy by the flexible elongated member 1 as the endoscope.

The elongated member main body H is connected to the imaging device IM via the first connector 13a. Light transmitted to the imaging device IM from the tip portion T via the image transmission portion 31 of the flexible elongated member 1 is processed by the imaging device IM. An image processed by the imaging device IM is displayed on the display device D. A known display device may be used for the display device D.

According to the embodiment, the light source device LS has an illumination light source LS1 and a laser light source LS2. The elongated member main body H is connected to the illumination light source LS1 via the third connector 13c. Light irradiated from the illumination light source LS1 such as an LED is transmitted to the tip portion T via the fiber bundle for illumination 33. Light transmitted to the fiber bundle for illumination 33 is irradiated from the tip of the fiber bundle for illumination 33, making it possible to illuminate the target site or the lumen to be observed.

The elongated member main body H is connected to the laser light source LS2 via the second connector 13b. Laser light output from the laser light source LS2 is transmitted to the tip portion T via the laser transmission portion 32. In this way, laser light for therapy is irradiated from the tip of the laser transmission portion 32, making it possible to subject the affected part to laser therapy. The output and the wavelength of the laser light to be output from the laser light source LS2 may be changed as needed in accordance with the therapy objective or the therapy method. For example, in a case of the photodynamic therapy (PDT), the output of the laser light may generally be set to approximately between 100 and 500 mW, or between 100 and 1000 mW, while the wavelength of the laser light may be set to a wavelength that makes it possible to excite a photosensitive drug, the wavelength being in the ultraviolet ray region (between 400 and 450 nm or in the neighborhood thereof) or in the infrared ray region (between 600 and 850 nm). A ruby laser, an alexandrite laser, a YAG laser, a dye laser, a diode laser, an excimer laser, or a fiber laser such as Yb (Ytterbium), for example, may be used as a laser to be output from the laser light source.

The image transmission portion 31 transmits light entering from the tip of the image transmission portion 31 to the imaging device IM. According to the embodiment, the image transmission portion 31 is an optical fiber extending from the proximal portion Pa (the first connector 13a side) of the flexible elongated member 1 to the tip portion T of the flexible elongated member 1. The image transmission portion 31 is configured by approximately 9,000 optical fibers to set the curvature radius to less than or equal to 10 mm, and, more preferably, to between 6 and 7 mm. The image transmission portion 31 transmits light irradiated from the tip of the fiber bundle for illumination 33 and reflected from an observation object to the imaging device IM. This makes it possible to cause an image of the lumen to be displayed on the display device D. The first tube 12a is covered with a resin, so that the optical fibers are not bare.

The laser transmission portion 32 transmits laser light output from the laser light source LS2 and irradiates the laser light from the tip of the laser transmission portion 32. According to the embodiment, the laser transmission portion 32 is an optical fiber extending from the proximal portion Pb (the second connector 13b side) of the flexible elongated member 1 to the tip portion T of the flexible elongated member 1. The laser transmission portion 32 may be configured by one or a plurality of optical fibers. The laser transmission portion 32 has the diameter of approximately 200 μm and preferably less than or equal to 150 μm. When the tip portion T of the flexible elongated member 1 reaches the target site, the laser light is irradiated from the laser transmission portion 32. The laser light from the laser transmission portion 32 causes a photosensitive substance accumulated in an affected part such as a tumor cell to produce a photochemical reaction to subject the affected part to therapy in a case of PDT and causes the affected part such as the tumor cell to undergo ablation in a case of ablation therapy. The second tube 12b is covered with a resin, so that the optical fibers are not bare.

The fiber bundle for illumination 33 irradiates light from the tip of the fiber bundle for illumination 33, the light being irradiated from the illumination light source LS1. According to the embodiment, the fiber bundle for illumination 33 is configured by a plurality of optical fibers extending from the proximal portion Pc side (the third connector 13c) of the flexible elongated member 1 to the tip portion T of the flexible elongated member 1. The fiber bundle for illumination 33 is configured by approximately between 150 and 300, or approximately less than 400 of optical fibers having the diameter of approximately between 30 and 50 μm. The light irradiated from the illumination light source LS1 is irradiated via the fiber bundle for illumination 33 and illuminates the target site for examination or therapy, or the lumen at the branch location to the target site to cause the target site or the lumen to be visually recognizable. The third tube 12c is covered with a resin, so that the plurality of optical fibers are not bare.

As shown in FIG. 2, the fiber bundle for illumination 33 is provided so as to fill the space between an inner surface 21a of the inner layer 21 of the below-described outer tube 2, an outer surface 31a of the image transmission portion 31, and an outer surface 32a of the laser transmission portion 32. Therefore, the image transmission portion 31, the laser transmission portion 32, and the fiber bundle for illumination 33 are filled inside the outer tube 2. In other words, the flexible elongated member 1 being the endoscope does not have a hand operating portion capable of changing the curving state of the tip portion T by a hand operation (on the proximal portion P side) and the curving direction of the tip portion T of the flexible elongated member 1 is changed by rotational operation in the circumferential direction of the axis of the flexible elongated member 1 by a hand operation. Therefore, an operating member such as a wire that extends to the tip portion T from the proximal portion P side of the flexible elongated member 1 to change the curving state of the tip portion T is not provided. Moreover, a physical channel through which a different member such as a guide wire is to be inserted is also not provided. The tip portion T of the flexible elongated member 1 is curved beforehand and the advancing direction of the flexible elongated member 1 is changed when the extending direction of the tip T is changed by rotating the flexible elongated member 1 in the circumferential direction of the axis thereof.

Figure 3:
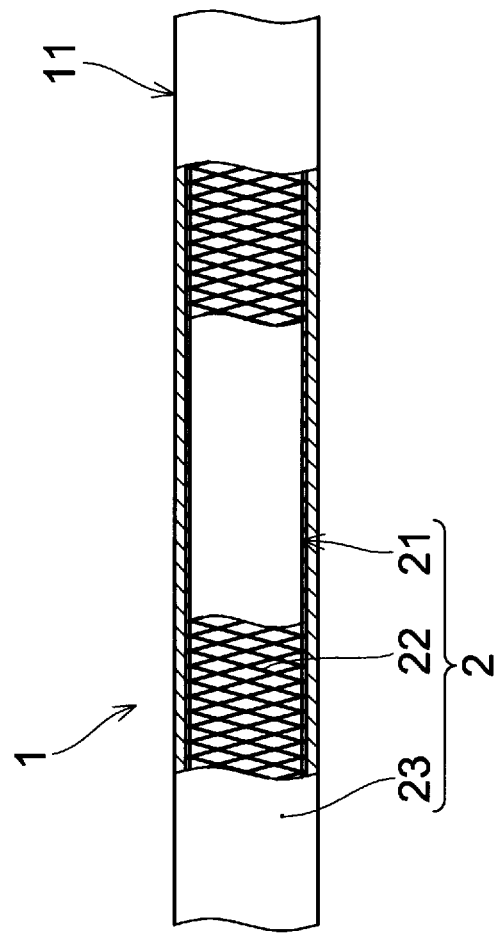
FIG. 3 shows an enlarged view of an area E in FIG. 1, showing the internal structure of an outer tube in FIG. 1.

The outer tube 2 is a tubular part being provided along the outer periphery of the optical element unit 3 and being positioned outer side of the flexible elongated member 1. According to the embodiment, as shown in FIG. 3, the outer tube 2 has an outer layer 23 mainly containing a resin having flexibility, the reinforcement layer 22 provided inside the outer layer 23, and the inner layer 21 configured by a resin having flexibility, the inner layer 21 covering the inside of the reinforcement layer 22. While the outer tube 2 is configured by the inner layer 21, the reinforcement layer 22, and the outer layer 23, it is not limited to the three-layer structure, so that the outer tube 2 may be configured by only the reinforcement layer 22 and the outer layer 23. For example, the outer layer 23 may be subjected to coating treatment, or the reinforcement layer 22 may be directly wound to the optical element unit 3 without providing the inner layer 21.

The inner layer 21 is a tubular layer configured by a resin having flexibility. The resin configuring the inner layer 21 includes Pebax, a polyamide-based elastomer, urethane, and nylon, for example. The inner layer 21 does not have to be formed. The optical element unit 3 is provided inside the inner surface 21a of the inner layer 21. The reinforcement layer 22 is formed by a reinforcement body such as a wire made of a metal being wound outside the inner layer 21 in a mesh shape. The reinforcement layer 22 being formed in a mesh shape allows the flexible elongated member 1 to have a predetermined rigidity. The reinforcement layer 22 may be a metal braid layer configuring a metal wire in a net shape, or a coil layer, for example, however, the reinforcement layer 22 is not limited to such examples. The outer layer 23 is a tubular covering layer to cover the reinforcement layer 22, and the outer layer 23 is configured by a resin having flexibility. The resin configuring the outer layer 23 includes Pebax, a polyamide-based elastomer, urethane, and nylon, for example. The outer layer 23 may be subjected to hydrophilic coating treatment.

The outer diameter of the outer tube 2 may be changed as needed in accordance with the use of the flexible elongated member 1. In a case that the endoscope is an endoscope for lung examination and/or therapy to be inserted toward a lung peripheral part (a bronchiole, a respiratory bronchiole), for example, the outer diameter of the outer tube 2 may be set to be preferably between 0.5 and 2.5 mm and more preferably between 0.8 and 1.5 mm.

According to the embodiment, in the flexible elongated member 1, when a rotating force in the circumferential direction of the axis of the flexible elongated member 1 is applied to a grip portion 4 provided between the tip portion T and the proximal portion P, the rotating force is transmitted to the tip portion T of the flexible elongated member 1 via an intermediate portion 5. Therefore, the tip portion T of the flexible elongated member 1 is positioned in a predetermined direction. For example, in a case that, at a location in a lumen up to a target site (such as an affected part to be observed), the orientation of the tip portion T of the flexible elongated member 1 is not directed in the direction toward a route up to the target site, a rotating force is applied such that a twist is applied by a hand operation to the grip portion 4 of the flexible elongated member 1 in the circumferential direction of the axis thereof. In this way, a rotating force applied to the grip portion 4 of the flexible elongated member 1 is transmitted to the tip portion T of the flexible elongated member 1 via the intermediate portion 5 and the tip portion T of the flexible elongated member 1 rotates in the circumferential direction of the axis thereof. When the tip portion T is oriented in the direction of the route up to the target site, the grip portion 4 of the flexible elongated member 1 is pushed manually to advance the tip portion T of the flexible elongated member 1 in the lumen. Moreover, when the flexible elongated member 1 is introduced into the lumen, a bronchoscope may be used as the introduction assisting tool U. At that time, the bronchoscope is inserted up to the main bronchus of the lung and the flexible elongated member 1 is inserted into the sheath of the bronchoscope. After the tip portion T of the flexible elongated member 1 reaches the tip of the bronchoscope inserted into the lumen, by further advancing the flexible elongated member 1 so as to extend from the bronchoscope, the tip portion T can reach a target position TS beyond a lobar bronchus.

According to the embodiment, the reinforcement layer 22 and the optical element unit 3 have a predetermined rigidity capable of transmitting a rotating force of the flexible elongated member 1 in the circumferential direction of the axis thereof and a pushing force in the axial direction of the flexible elongated member 1. Because of a predetermined rigidity of the reinforcement layer 22 provided inside the outer tube 2 and the optical element unit 3 provided along the axial direction of the outer tube 2 inside the reinforcement layer 22, the rotating force applied at the grip portion 4 of the flexible elongated member 1 may be transmitted to the tip portion T of the flexible elongated member 1 via the intermediate portion 5, so that the tip portion T of the flexible elongated member 1 easily rotates in the circumferential direction of the axis of the outer tube 2. Therefore, it is easy to operate the tip portion T of the flexible elongated member 1 in a desired direction and it is easy to advance the flexible elongated member 1 toward the target site at the branch location of the lumen. Moreover, the reinforcement layer 22 and the optical element unit 3 having a predetermined rigidity makes it possible to transmit a pushing force being applied to the grip portion 4 of the flexible elongated member 1 to the tip portion T of the elongated member 1 so that the tip portion T of the flexible elongated member 1 easily advances.

Moreover, according to the embodiment, the reinforcement layer 22 and the optical element unit 3 have flexibility capable of curving along a route of a branch of a lumen while holding the shape of the tip portion T of the flexible elongated member 1. The reinforcement layer 22 and the optical element unit 3 have a predetermined rigidity as described in the above, so that a predetermined shape may be held in a case that an external force is not applied to the tip portion T of the flexible elongated member 1, and the shape of the tip portion T stabilizes to allow the tip portion T of the flexible elongated member 1 to be easily adjusted in the direction toward the target site at the branch location of the lumen. Furthermore, the reinforcement layer 22 and the optical element unit 3 have a predetermined flexibility, so that a portion from the tip portion T of the flexible elongated member 1 to the proximal portion P thereof can curve along the route of the branch of the lumen to be deformed. In the body, the body cavity is normally branched, so that, if rigidity of the flexible elongated member 1 is too high, the flexible elongated member 1 may press the wall portion of the lumen at a portion ahead of the branch and at a portion behind the branch at the time of advancing of the flexible elongated member 1. However, since the flexible elongated member 1 has flexibility capable of deforming according to a curvature along the route of the branch of the lumen, pressing of the wall portion of the lumen may be prevented. Therefore, slidability in the lumen is improved. Therefore, even in a case of a large curvature of the lumen, insertion of the flexible elongated member 1 thereinto is possible, also reducing the burden on the lumen. For example, according to the embodiment, when the reinforcement layer 22 and the optical element unit 3 are inserted toward a lung peripheral part from a branch location in a bronchus of the lung, they have flexibility capable of curving along the curvature of the branch location. In this way, in a case that the flexible elongated member 1 is an endoscope for lung examination and/or therapy, the flexible elongated member 1 may be advanced along a route branching in a complex manner in the lung peripheral part from the lung bronchus, making it possible to carry out examination and/or therapy in the lung peripheral part. Moreover, in a case that the endoscope is inserted into a bronchoscope, flexibility of the flexible elongated member 1 does not impede the curving operation of the bronchoscope in a case that the tip of the bronchoscope is subjected to a curving operation, for example.

The flexible elongated member 1 is capable of curving along a complex branch of the lung, for example, the flexible elongated member 1 may curve with 90 degrees or greater, such as 180 degrees, while maintaining a bend radius of less than or equal to 10 mm, for example, between 6 and 7 mm. The bend radius of the flexible elongated member 1 may be decreased such that the flexible elongated member 1 may advance to a desired branched lumen at a branch of a lumen. The flexible elongated member 1 has flexibility capable of curving along the shape of a bronchus and rigidity capable of selecting a target branched lumen while holding the curvature shape and adjusting position of the tip portion T. To move to a target branched lumen to reach the target site, the flexible elongated member 1 positions the tip portion T thereof at a branch to an opening of the target branched lumen to advance the tip portion T thereof to the target branched lumen. In a case that rigidity of the flexible elongated member 1 is low, the tip portion T is hard to be positioned with respect to the opening of the target branched lumen at a branch due to the flexibility. However, as the flexible elongated member 1 has rigidity in addition to flexibility, it can position the tip portion T thereof to the opening of the target branched lumen at a branch and can advance the tip portion T thereof to the target branched lumen.

Moreover, the space between the inner surface 21a of the inner layer 21 of the flexible elongated member 1, the outer surface 31a of the image transmission portion 31, and the outer surface 32a of the laser transmission portion 32 are filled by the fiber bundle for illumination 33. Furthermore, as described in the above, the flexible elongated member 1 is not provided with a physical channel to insert therethrough a different member such as a guide wire, or an operating member such as a wire, the operating member extending to the tip portion T from the proximal portion P of the flexible elongated member 1 to operate the tip portion T of the flexible elongated member 1 by a hand operation with a hand operating portion. Therefore, the outer diameter of the endoscope does not increase, making it possible to decrease the diameter of the endoscope. Thus, the endoscope may be easily inserted into a lumen having a narrow portion into which insertion of the endoscope is difficult, such as a lung peripheral part (a bronchiole, a respiratory bronchiole).

Next, an operation method of the endoscope according to the embodiment is described with a therapy method (PDT) of lung cancer being generated in a bronchiole or a respiratory bronchiole as an example.

Figure 4:
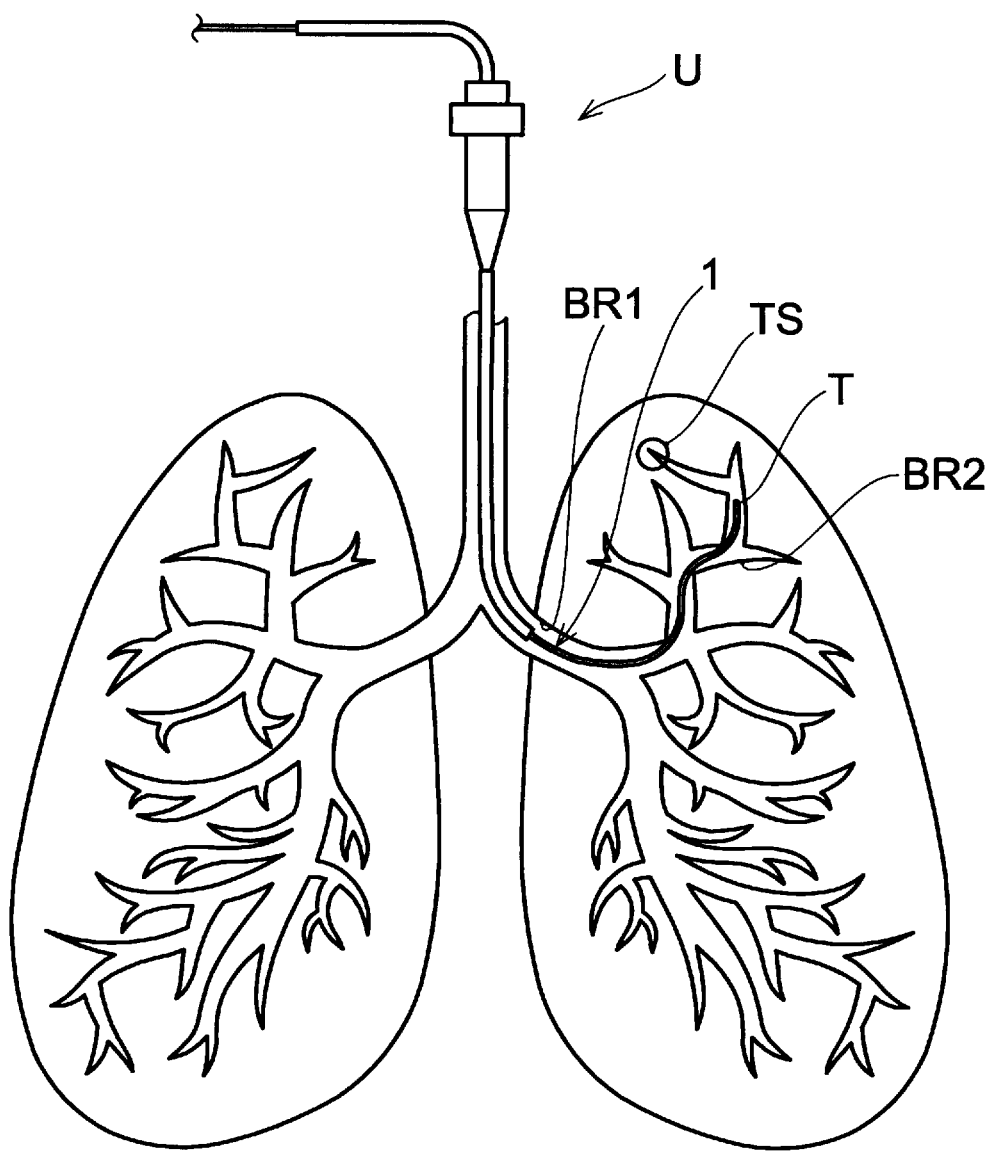
FIG. 4 schematically shows the tip of the endoscope according to one embodiment of the invention being introduced into a bronchiole of the lung.
Figure 5:
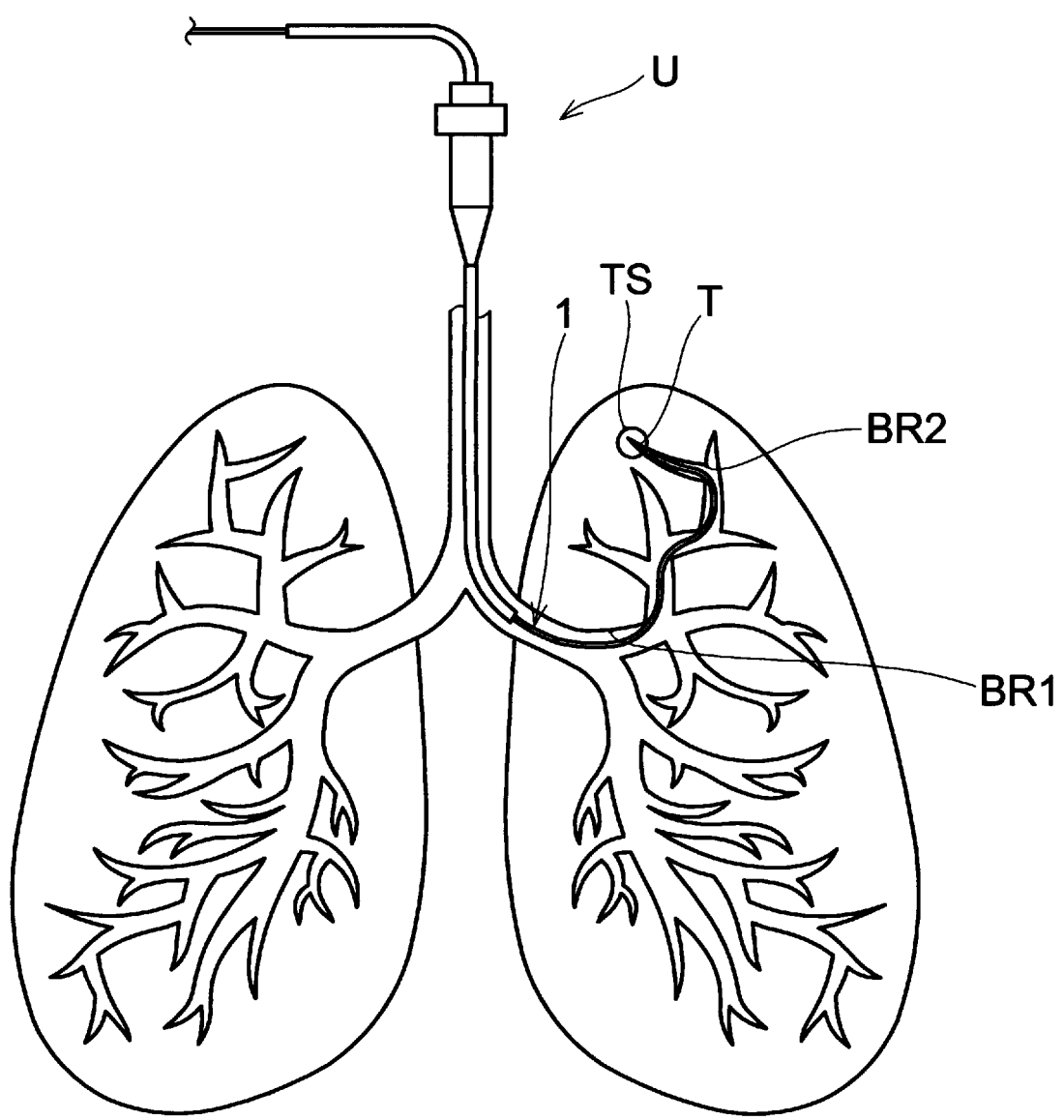
FIG. 5 schematically shows a view of the tip of the endoscope according to one embodiment of the invention reaching the position of a tumor cell.
Figure 6:
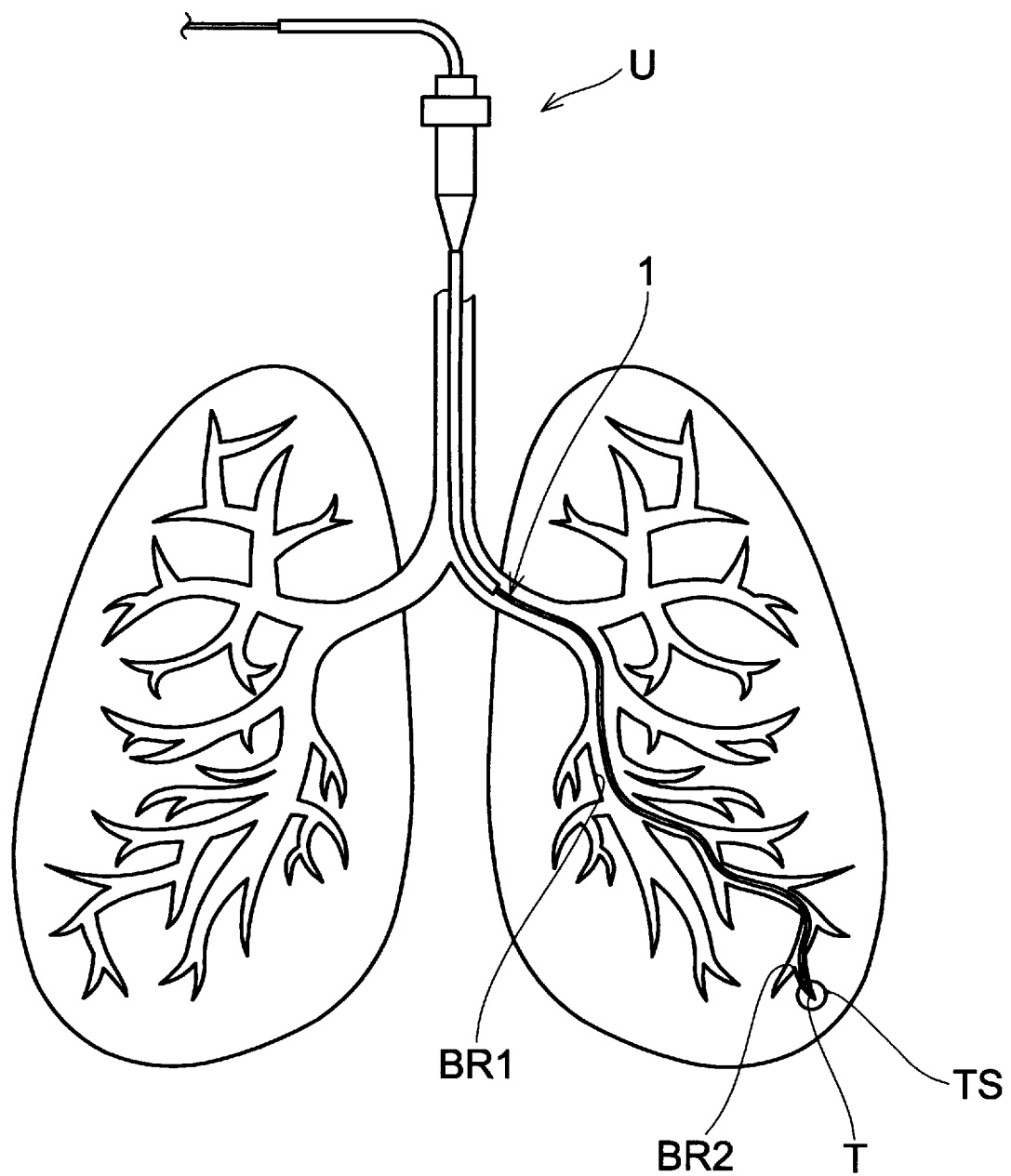
FIG. 6 schematically shows another view of the tip of the endoscope according to one embodiment of the invention reaching the position of the tumor cell.

First, a photosensitive substance such as a substance having oncotropicity and photosensitivity, for example, laserphyrin (registered trademark) or photofrin (registered trademark) is administered to a lung cancer patient. After the photosensitive substance accumulates in a tumor cell of lung cancer, a flexible elongated member 1 being an endoscope is moved to a bronchiole BR2 via a bronchus BR1 as shown in FIG. 4. At a branch location of the bronchiole BR2 of the lung, a practitioner moves a tip portion T of the flexible elongated member 1 toward a target site TS while checking an image being transmitted from an image transmission portion 31 and being displayed on a display device D (see FIG. 1). The tip portion T of the flexible elongated member 1 may be shaped such that the tip portion T curves slightly before being inserted into a lumen of the patient. As described in the above, the endoscope has a predetermined rigidity caused by a reinforcement layer 22 and a light element unit 3, making it easy to adjust position of the tip portion T of the flexible elongated member 1 of the endoscope at the branch location of the bronchiole BR2 of the lung and making it possible to cause the flexible elongated member 1 to reach the target site TS as shown in FIG. 5.

Laser light having a predetermined wavelength being irradiated from a laser transmission portion 32 of the endoscope, in a case that a site being irradiated is a tumor cell, causes the photosensitive substance being accumulated in the tumor cell to emit fluorescence. This completes specifying the site of the tumor cell by photodynamic diagnosis (PDD). After the tumor cell is specified, the wavelength of the laser light is changed by a light source device LS and the laser light is irradiated to the tumor cell emitting fluorescence. Therefore, a photodynamic reaction is produced to bring about the necrosis of the tumor cell due to a strong oxidation action. This makes it possible to carry out therapy of a tumor generated in the bronchiole BR2 of the lung, or a respiratory bronchiole being further branched from the bronchiole BR2 thereof.

DESCRIPTION OF REFERENCE NUMERALS

1 FLEXIBLE ELONGATED MEMBER
12a FIRST TUBE
12b SECOND TUBE
12c THIRD TUBE
13a FIRST CONNECTOR
13b SECOND CONNECTOR
13c THIRD CONNECTOR
2 OUTER TUBE
21 INNER LAYER
21a INNER SURFACE OF INNER LAYER
22 REINFORCEMENT LAYER
23 OUTER LAYER
3 OPTICAL ELEMENT UNIT
31 IMAGE TRANSMISSION PORTION
31a OUTER SURFACE OF IMAGE TRANSMISSION PORTION
32 LASER TRANSMISSION PORTION
32a OUTER SURFACE OF LASER TRANSMISSION PORTION
33 FIBER BUNDLE FOR ILLUMINATION
4 GRIP PORTION
5 INTERMEDIATE PORTION
6 JUNCTION
B SYSTEM MAIN BODY
BR1 BRONCHUS
BR2 BRONCHIOLE
C CONTROL DEVICE
D DISPLAY DEVICE
H ELONGATED MEMBER MAIN BODY
IM IMAGING DEVICE
LS LIGHT SOURCE DEVICE
LS1 ILLUMINATION LIGHT SOURCE
LS2 LASER LIGHT SOURCE
P PROXIMAL PORTION OF FLEXIBLE ELONGATED MEMBER
Pa PROXIMAL PORTION OF FLEXIBLE ELONGATED MEMBER ON FIRST TUBE SIDE
Pb PROXIMAL PORTION OF FLEXIBLE ELONGATED MEMBER ON SECOND TUBE SIDE
Pc PROXIMAL PORTION OF FLEXIBLE ELONGATED MEMBER ON THIRD TUBE SIDE
S ENDOSCOPE SYSTEM
T TIP PORTION OF FLEXIBLE ELONGATED MEMBER
TS TARGET SITE
U INTRODUCTION ASSISTING TOOL

The invention claimed is:

1. An endoscope comprising a flexible elongated member having a tip portion and a proximal portion, the flexible elongated member comprising an elongated outer tube to be inserted into a lumen to be observed and an optical element unit provided inside the outer tube,
wherein the flexible elongated member has a grip portion provided between the tip portion and the proximal portion,
the flexible elongated member has an intermediate portion being between the tip portion and the grip portion,
wherein the tip portion is configured to be shapable into a curving state,
when a rotating force in a circumferential direction of an axis of the flexible elongated member and a pushing force are applied to the grip portion, the rotating force and the pushing force are transmitted to the tip portion via the intermediate portion to position the tip portion in a predetermined direction,
wherein the outer tube has, at the tip portion and the intermediate portion, an outer layer mainly containing a resin having flexibility and a reinforcement layer provided inside the outer layer, the optical element unit has, at the tip portion and the intermediate portion, an optical fiber for image transmission, a laser transmission portion, and a fiber bundle for illumination, the flexible elongated member has, at the tip portion and the intermediate portion, rigidity capable of being inserted into a target branched lumen from a branch of the lumen while maintaining the shape and adjust position of the tip portion, and flexibility capable of curving along a route to the target branched lumen, and the fiber bundle for illumination is configured, at the tip portion and the intermediate portion, by a plurality of optical fibers which are provided so as to fill the space between an inner surface of the outer tube, an outer surface of the optical fiber for image transmission, and an outer surface of the laser transmission portion, wherein the endoscope does not have an operating wire for performing a curving action on the tip portion.

2. The endoscope according to claim 1, wherein an inserted part of the flexible elongated member to be inserted into the lumen to be observed has the outer diameter of between 0.5 and 2.5 mm.

3. The endoscope according to claim 1, wherein the rigidity and the flexibility of the flexible elongated member are caused by a rigidity or a flexibility of at least either one of the reinforcement layer and the optical element unit.

4. An endoscope comprising a flexible elongated member having a tip portion and a proximal portion, the flexible elongated member comprising an elongated outer tube to be inserted into a lumen to be observed and an optical element unit provided inside the outer tube, wherein the flexible elongated member has a grip portion provided between the tip portion and the proximal portion, the flexible elongated member has an intermediate portion being between the tip portion and the grip portion, wherein the tip portion is configured to be shapable into a curving state, when a rotating force in a circumferential direction of an axis of the flexible elongated member and a pushing force are applied to the grip portion, the rotating force and the pushing force are transmitted to the tip portion via the intermediate portion to position the tip portion in a predetermined direction, wherein the outer tube has, at the tip portion and the intermediate portion, an outer layer mainly containing a resin having flexibility and a reinforcement layer provided inside the outer layer, the optical element unit has, at the tip portion and the intermediate portion, an optical fiber for image transmission, and a fiber bundle for illumination, the flexible elongated member has, at the tip portion and the intermediate portion, rigidity capable of being inserted into a target branched lumen from a branch of the lumen while maintaining the shape and adjust position of the tip portion, and flexibility capable of curving along a route to the target branched lumen, and the fiber bundle for illumination is configured, at the tip portion and the intermediate portion, by a plurality of optical fibers which are provided so as to fill the space between an inner surface of the outer tube, and an outer surface of the optical fiber for image transmission, wherein the endoscope does not have an operating wire for performing a curving action on the tip portion.

\* \* \* \* \*